US006187969B1

(12) United States Patent
Yamaguchi et al.

(10) Patent No.: US 6,187,969 B1
(45) Date of Patent: Feb. 13, 2001

(54) PROCESS FOR PRODUCING FLUOROALCOHOL

(75) Inventors: Fumihiko Yamaguchi; Shoji Takaki; Toru Yoshizawa; Eiji Ogura; Toshiyuki Katsube, all of Settsu (JP)

(73) Assignee: Daikin Industries, Ltd., Osaka-fu (JP)

( * ) Notice: Under 35 U.S.C. 154(b), the term of this patent shall be extended for 0 days.

(21) Appl. No.: 09/394,679

(22) Filed: Sep. 13, 1999

(30) Foreign Application Priority Data

Mar. 15, 1999 (JP) .................................................. 11-068932

(51) Int. Cl.[7] .......................... C07C 29/00; C07C 29/32; C07C 29/44; C07C 29/80; C07C 29/88
(52) U.S. Cl. ........................................... 568/842; 568/904
(58) Field of Search ..................................... 568/842, 904

(56) References Cited

U.S. PATENT DOCUMENTS 3,927,129  12/1975  Haszeldine et al. .............. 260/653.1
5,023,377 * 6/1991  Desmarteau et al. ................ 564/301

FOREIGN PATENT DOCUMENTS

0524638A2   1/1993  (EP) .
0967193A2  12/1999  (EP) .

* cited by examiner

*Primary Examiner*—Peter O'Sullivan
(74) *Attorney, Agent, or Firm*—Larson & Taylor PLC

(57) ABSTRACT

A process for producing a fluoroalcohol of the following formula (1)

$$H(CFR^1CF_2)_nCH_2OH \qquad (1)$$

(n=1 or 2, wherein $R^1$ represents F or $CF_3$ when n=1; $R^1$ represents F when n=2) comprising reacting methanol with tetrafluoroethylene or hexafluoropropylene in the presence of an initiator wherein the fluoroalcohol of formula (1) is distilled after decomposing the remaining initiator contained in the reaction mixture.

3 Claims, No Drawings

PROCESS FOR PRODUCING FLUOROALCOHOL

FIELD OF THE INVENTION

This invention relates to a process for producing a fluoroalcohol of the general formula (1):

$$H(CFR^1CF_2)_nCH_2OH \qquad (1)$$

(n=1 or 2, wherein $R^1$ represents F or $CF_3$ when n=1; $R^1$ represents F when n=2).

BACKGROUND ART

Regarding the technology of producing $H(CF_2CF_2)_nCH_2OH$ (n=1 or 2), Japanese Unexamined Patent Publication No. 154707/1979 and U.S. Pat. No. 2,559,628 disclose that a mixture of telomers comprising $H(CF_2CF_2)_nCH_2OH$ (n=12 at a maximum) is prepared by reacting methanol with tetrafluoroethylene in the presence of t-butyloctyl peroxide.

However, even if the telomer mixture obtained by the process is purified by distillation, the evaporation residue of the order of about a few hundreds of ppm can not be eliminated. When it is used as a solvent in the manufacture of an information recording medium comprising a substrate sheet and as built thereon a recording layer adapted for laser information writing and/or reading, such as CD-R and DVD-R, the disadvantage is inevitable that a high quality information recording medium can not be obtained owing to the influence of said evaporation residue.

DISCLOSURE OF THE INVENTION

It is an object of the invention to provide a process for producing a fluoroalcohol of the following general formula (1)

$$H(CFR^1CF_2)_nCH_2OH \qquad (1)$$

(wherein n and $R^1$ are as defined above), which is substantially free of impurities such as an evaporation residue and UV-absorbing substances.

The inventors found that when the fluoroalcohol of general formula (1) is distilled after elimination, by decomposition, of the remaining initiator in the reaction mixture, the above object is accomplished. The present invention has been completed based on this novel finding.

The invention relates to the following processes.

1. A process for producing a fluoroalcohol of the following formula (1)

$$H(CFR^1CF_2)_nCH_2OH \qquad (1)$$

(n=1 or 2, wherein $R^1$ represents F or $CF_3$ when n=1; $R_1$ represents F when n=2) comprising reacting methanol with tetrafluoroethylene or hexafluoropropylene in the presence of an initiator, wherein the fluoroalcohol of formula (1) is distilled after decomposing the remaining initiator contained in the reaction mixture.

2. The process according to item 1 above wherein the decomposition of the remaining initiator is carried out using at least one means selected from the group consisting of decomposition of the remaining initiator by heating the reaction mixture, decomposition of the remaining initiator by contact with an acid catalyst, decomposition of the remaining initiator by contact with a reducing agent, decomposition of the remaining initiator by UV irradiation and decomposition of the remaining initiator by contact with a base.

3. The process according to item 1 above wherein the distillate containing the fluoroalcohol of formula (1) is further distilled either in the presence of a base or after contact of said distillate with a base.

In the reaction of methanol with tetrafluoroethylene or hexafluoropropylene in the presence of an initiator, methanol is used in excess over tetrafluoroethylene or hexafluoropropylene. The reaction temperature is about 40–140° C., the reaction time is about 3–12 hours, and the reaction pressure is about 0.2–1.2 MPa. The reaction may be conducted in a high pressure reactor such as autoclave. The reaction system is preferably subjected to inert gas purge using nitrogen, argon or the like gas. The reaction is generally carried out batchwise.

Examples of initiator include peroxides and azo compounds. It is preferable to use an initiator with a half-life of about 0.5–10 hours at a reaction temperature.

Preferred examples of initiator include di-t-butyl peroxide (available under the tradename "perbutyl D", manufacture of NOF Corp.), t-butylperoxy-2-ethyl hexanoate (available under the tradename "perbutyl O", manufacture of NOF Corp.), t-butylperoxyisopropyl carbonate (available under the tradename "perbutyl I", manufacture of NOF Corp.) and like peroxides; and azobisisobutyronitrile, azobiscyclohexanenitrile and like azo compounds.

The amount of the initiator is generally about 0.005–0.1 mole per mole of tetrafluoroethylene or hexafluoropropylene.

The above reaction may be carried out in the presence of an acid acceptor. Examples of acid acceptor include calcium carbonate, magnesium carbonate, sodium carbonate, potassium carbonate, barium carbonate, sodium bicarbonate, potassium bicarbonate and like carbonates and bicarbonates of alkali metals or alkaline earth metals; calcium oxide, calcium hydroxide and soda lime. Preferred acid acceptors are substances capable of capturing the acid generated during the reaction (e.g., HF) without imparting strong basicity to the reaction mixture.

The amount of the acid acceptor is not specifically limited to, but may be about 0.001–0.1 mole per mole of tetrafluoroethylene or hexafluoropropylene.

The process of the invention optionally includes a distillation step for removing any excess of methanol from the reaction mixture after completion of the reaction.

The means for decomposing the undecomposed initiator remaining in the reaction mixture is not specifically limited to, and the examples of the means include following (i)–(v).

In the following (ii), (iii) and (v), "contact" is carried out by adding an acid catalyst, reducing agent or base to the reaction mixture.

(i) Decomposition by Heating

The temperature to heat the reaction mixture can be suitably selected according to the kind of the initiator, and is generally about 100–200° C. Heating is performed, either in an open system or in a closed system, for about 0.5–10 hours.

(ii) Decomposition by Contact with an Acid Catalyst

The acid catalyst may be an inorganic acid, an organic acid or a solid acid catalyst.

Examples of inorganic acid include sulfuric acid, hydrochloric acid, nitric acid, hydroiodic acid and hydrobromic acid. Examples of organic acid include acetic acid and trifluoromethanesulfonic acid. Examples of solid acid catalyst include silica alumina, silica magnesia and ion exchange resins or ion exchange membranes having sulfonic, carboxyl and like acidic groups. A preferred example of the ion exchange membrane is NAFION (tradename, manufacture of E.I.duPont de Nemours and Company, perfluorosulfonic acid ionomer).

These acid catalysts can be used singly or in combination.

The amount of the acid catalyst can be suitably selected according to the amount of the initiator added to the reaction system and the reaction conditions, but is generally about 1–500 parts by weight based on 100 parts by weight of the initiator added.

The condition for decomposing the remaining initiator by the acid catalyst can be suitably selected according to the kind of the initiator and the acid catalyst. The decomposition by the acid catalyst is generally carried out at about 0–100° C. for about 0.5–20 hours, either in an open system or in a closed system.

(iii) Decomposition by Contact with a Reducing Agent

Examples of reducing agent include Fe(II) salts, Cr(II) salts, Cu(I) or Cu(II) salts, Ag(I) salts and like salts of transition metals, and thiosulfates. More specifically, $FeSO_4$, $CrCl_2$, $CuCl$, $Cu(OCOCH_3)_2$, $[Ag(NH_3)_2]OH$ and $Na_2S_2O_3$ can be mentioned. These reducing agents can be used singly or in combination.

The amount of the reducing agent can be suitably selected according to the amount of the initiator added to the reaction system and the reaction conditions, but is generally about 0.001–5 moles per mole of the initiator added.

The condition for decomposing the remaining initiator by the reducing agent can be suitably selected according to the kind of the initiator and the reducing agent. The decomposition by the reducing agent is generally carried out at about 20–100° C. for 0.5–10 hours, either in an open system or in a closed system.

(iv) Decomposition by UV Irradiation

The UV decomposition may be carried out by irradiating the reaction mixture with UV light (at about 100–390 nm) for about 0.5–10 hours. The wavelength of the irradiating UV light can be suitably selected according to the kind of initiator. The UV irradiation can be carried out using, for example, an ultra-high-pressure mercury lamp, a high-pressure mercury lamp, a medium-pressure mercury lamp or a low-pressure mercury lamp.

(v) Decomposition by Contact with a Base

Examples of base include sodium carbonate, potassium carbonate and like alkali metal carbonates; sodium bicarbonate, potassium bicarbonate and like alkali metal bicarbonates; sodium methoxide, sodium ethoxide, sodium propoxide, potassium t-butoxide, lithium ethoxide and like alkali metal alkoxides; sodium hydroxide, potassium hydroxide, lithium hydroxide and like alkali metal hydroxides; calcium hydroxide, barium hydroxide, magnesium hydroxide and like alkaline earth metal hydroxide; aluminum hydroxide and soda lime.

These bases can be used singly or in combination.

The amount of the base can be suitably selected according to the amount of the initiator added to the reaction system and the reaction conditions, but is generally about 0.001–5 moles per mole of the initiator added.

The condition for decomposing remaining initiator by the base can be suitably selected according to the kind of the initiator and the base.

The decomposition by the base is generally arried out at about 20–100° C. for about 0.5–10 hours, either in an open system or in a closed system.

Alternatively, the distillation of the fluoroalcohol of formula (1) may be carried out immediately after the addition of the base.

When the decomposition of the remaining initiator is performed by contact with a base, the amount of the impurities, included in the resulting fluoroalcohol of the general formula (1), is reduced to a greater degree without the further distillation either in the presence of a base or after contact of the distillate containing the fluoroalcohol of the formula (1) with a base. The "further distillation" is mentioned below.

The decomposition of the remaining initiator may be carried out batchwise or continuously.

The above means for decomposing the remaining initiator can be used in a combination of two or more kinds.

In the process for decomposing the remaining initiator according to the invention, it is preferable to decompose the remaining initiator thoroughly, but it is sufficient that the concentration of the remaining initiator in the reaction mixture after the treatment be about 1,000 mass ppm or less, preferably about 50 mass ppm or less. The concentration of the remaining reaction initiator is calculated based on the total amount of the reaction mixture which comprises excess of methanol.

After decomposition of the remaining initiator, the fluoroalcohol of the general formula (1) $H(CFR^1CF_2)_nCH_2OH$ (1) (n and $R^1$ are as defined above) is distilled for purifying, i.e., for removing other impurities present in the reaction mixture, such as methanol, $H(CF_2CF_2)_nCH_2OH$ (n≧3) and $H(CF(CF_3)CF_2)_nCH_2OH$ (n≧2).

The distillation for purifying may be carried out batchwise or continuously.

In the process of the invention, after the above distillation for purification, the purified fluoroalcohol of the formula (1) $H(CFR^1CF_2)_nCH_2OH$ (1) (n and $R^1$ are as defined above), i.e., the distillate containing the fluoroalcohol of the formula (1), is further distilled either in the presence of a base or after contact of the said distillate with a base. Examples of base to be added to the above fluoroalcohol distillate or contacted therewith include the bases mentioned in the above (v). The amount of the base is about 0.05–1.0 mole, preferably about 0.1–0.5 mole, per kg of the distillate containing fluoroalcohol of general formula (1).

The distillation either in the presence of a base or after contact of the distillate with a base may be carried out batchwise or continuously.

According to the process of the invention, there can be provided a fluoroalcohol of the general formula (1) with an evaporation residue of 50 ppm or less, preferably 25 ppm or less, more preferably 10 ppm or less.

The amount of the evaporation residue can be determined as follows. Thus, the fluoroalcohol is evaporated at 40° C. under 5 mmHg and the residue is weighed and expressed in mass ppm based on the fluoroalcohol.

The UV absorbance in methanol at 205 nm of the fluoroalcohol of general formula (1) as obtained according to the invention is not greater than −0.1 abs, preferably −0.1 abs or less, more preferably −0.2 abs or less. The UV absorbance in methanol can be measured using a mixture of 1 ml of the fluoroalcohol of general formula (1) and 3 ml of methanol as a sample and methanol as a reference.

That the fluoroalcohol provided according to the process of the invention is "substantially free of impurity" means that (i) the residue on evaporation of the fluoroalcohol is not more than 50 ppm, preferably 25 ppm or less, more preferably 10 ppm or less and/or (ii) the UV absorbance (at 205 nm) thereof in methanol is not more than 0.1 abs, preferably −0.1 abs or less, more preferably −0.2 abs or less.

The information recording medium comprising a substrate sheet and as built thereon a recording layer adapted for laser information writing and/or reading can be manufactured by dissolving a dye in a solvent containing the fluoroalcohol of general formula (1) according to the invention, preferably a fluorine-containing solvent comprising said fluoroalcohol and, using the resulting dye solution, carrying out the routine series of operations inclusive of coating a substrate with it and drying the coated substrate to provide a dye-containing recording layer. Examples of dye include cyanine dyes, phthalocyanine dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes, and metal complex dyes. Examples of raw material for the substrate sheet include polycarbonates, poly(methyl methacrylate), epoxy resin, amorphous polyolefins, polyesters, poly(vinyl chloride) and like plastics, glass and ceramics. For the purpose of improving surface smoothness and adhesion or preventing degradation of the recording layer, an undercoat may be provided between the recording layer and the substrate sheet and/or a protective layer may be formed on the recording layer.

According to the invention, there can be easily provided substantially impurity-free $HCF_2CF_2CH_2OH$, $H(CF_2CF_2)_2CH_2OH$ and $HCF(CF_3)CF_2CH_2OH$ which are suited for use in the manufacture of an information recording medium comprising a substrate sheet and as built thereon a recording layer adapted for laser information writing and/or reading (e.g., optical disks such as CD-R, DVD-R, etc.) or photosensitive material for film.

BEST MODE FOR CARRYING OUT THE INVENTION

The following examples illustrate the invention in further detail.

EXAMPLE 1

Calcium carbonate (30 g) was placed in an autoclave. The atmosphere inside the autoclave was replaced with nitrogen, which was then sucked with a vacuum pump. Methanol (2 L), tetrafluoroethylene and dit-butyl peroxide (45 g) as an initiator, were added to the autoclave. The reaction mixture was allowed to react for 6 hours at a temperature of 125° C. under a pressure of 0.8 MPa. The concentration of remaining di-t-butyl peroxide in the reaction mixture was analyzed by gas chromatography (SE-30, 3 m), and found to be 1.86%.

Thereafter, the reaction mixture was stirred at 140° C. for 3 hours so that the remaining di-t-butyl peroxide was decomposed. The concentration of remaining di-t-butyl peroxide was determined by gas chromatography, and found to be below detection limit (10 ppm). After being cooled, the reaction mixture was distilled to remove methanol therefrom. The reaction mixture was further distilled to separate $H(CF_2CF_2)_nCH_2OH$ (n is an integer of at least 2) from the mixture, giving a distillate of $HCF_2CF_2CH_2OH$ (1.2 L). The concentration of the evaporation residue of the resulting $HCF_2CF_2CH_2OH$ distillate was 20 ppm, and its UV absorbance (205 nm) was −1.0 abs.

Comparative Example 1

The procedure of Example 1 was repeated with the exception that the reaction mixture was not stirred at 140° C. for 3 hours. The concentration of the evaporation residue of the resulting $HCF_2CF_2CH_2OH$ distillate was 590 ppm, and its UV absorbance (205 nm) was 2.0 abs.

EXAMPLE 2

The procedure of Example 1 was repeated with the exception of adding $H_2SO_4$ (40 g) and stirring the reaction mixture at room temperature for 5 hours instead of stirring the reaction mixture at 140° C. for 3 hours to decompose the remaining initiator. The concentration of the evaporation residue of the resulting $HCF_2CF_2CF_2OH$ distillate was 22 ppm, and its UV absorbance (205 nm) was −1.0 abs.

EXAMPLE 3

The procedure of Example 1 was repeated with the exception of adding NAFION (135 g) and stirring at 70° C. for 1.5 hours instead of stirring the reaction mixture at 140° C. for 3 hours to decompose the remaining initiator. The concentration of the evaporation residue of the resulting $HCF_2CF_2CH_2OH$ distillate was 19 ppm, and its UV absorbance (205 nm) was −1.0 abs.

EXAMPLE 4

The procedure of Example 2 was repeated with the exception of using t-butylperoxy-2-ethylhexanoate (67 g) in place of di-t-butyl peroxide (45 g) and using $FeSO_4$ (94 g) in place of $H_2SO_4$ (40 g) to decompose the remaining initiator with stirring. The concentration of the evaporation residue of the resulting $HCF_2CF_2CH_2OH$ distillate was 19 ppm, and its UV absorbance (205 nm) was −1.0 abs.

EXAMPLE 5

The procedure of Example 1 was repeated with the exception that the reaction mixture was stirred at 50° C. for 4 hours under irradiation with a high-pressure mercury lamp (100 W) instead of being stirred at 140° C. for 3 hours to decompose the remaining initiator. The concentration of the evaporation residue of the resulting $HCF_2CF_2CH_2OH$ distillate was 21 ppm, and its UV absorbance (205 nm) was −1.0 abs.

EXAMPLE 6

The procedure of Example 4 was repeated with the exception that NaOH (27 g) was added to the reaction mixture in place of $FeSO_4$ (94 g) to decompose the remaining initiator with stirring. The concentration of the evaporation residue of the resulting $HCF_2CF_2CH_2OH$ distillate was 18 ppm, and its UV absorbance (205 nm) was −1.0 abs.

EXAMPLE 7

The procedure of Example 1 was repeated to carry out the reaction, decomposition of the remaining initiator and distillation. The resulting distillate of $H(CF_2CF_2)_nCH_2OH$ (n is an integer of at least 2) was further distilled and separated, giving $H(CF_2CF_2)_2CH_2OH$ as a distillate. The concentration of the evaporation residue of the resulting distillate of $H(CF_2CF_2)_2CH_2OH$ was 25 ppm, and its UV absorbance (205 nm) was −1.0 abs.

EXAMPLE 8

The procedure of Example 1 was repeated with the exception of using hexafluoropropylene in place of tetrafluoroethylene to carry out a reaction, decomposition of the remaining initiator and purification by distillation. The concentration of the evaporation residue of the resulting $HCF(CF_3)CF_2CH_2OH$ was 25 ppm, and its UV absorbance (205 nm) was −1.0 abs.

EXAMPLE 9

The procedure of Example 1 was repeated with the exception of adding 28% sodium methoxide (30 g) to the reaction mixture and distilling the mixture. The concentration of the evaporation residue of the resulting HCF$_2$CF$_2$CH$_2$OH distillate was 10 ppm, and its UV absorbance (205 nm) was −2.0 abs.

What is claimed is:

1. A process for producing a fluoroalcohol of the following formula (1)

$$H(CFR^1CF_2)_nCH_2OH \qquad (1)$$

(n=1 or 2, wherein R$^1$ represents F or CF$_3$ when n=1; R$_1$ represents F when n=2) comprising reacting methanol with tetrafluoroethylene or hexafluoropropylene in the presence of an initiator wherein the fluoroalcohol of formula (1) is distilled after decomposing the remaining initiator contained in the reaction mixture.

2. The process according to claim 1 wherein the decomposition of the remaining initiator is carried out using at least one means selected from the group consisting of decomposition of the remaining initiator by heating the reaction mixture, decomposition of the remaining initiator by contact with an acid catalyst, decomposition of the remaining initiator by contact with a reducing agent, decomposition of the remaining initiator by UV irradiation and decomposition of the remaining initiator by contact with a base.

3. The process according to claim 1 wherein the distillate containing the fluoroalcohol of formula (1) is further distilled either in the presence of a base or after contact of the said distillate with a base.

* * * * *